(12) United States Patent
Ranjbar et al.

(10) Patent No.: US 8,414,490 B2
(45) Date of Patent: Apr. 9, 2013

(54) SYSTEM AND METHOD FOR MODELLING LEFT VENTRICLE OF HEART

(76) Inventors: Saeed Ranjbar, Tehran (IR); Mersedeh Karvandi, Theran (IR); Mahdi Ajzachi, Tehran (IR)

( * ) Notice: Subject to any disclaimer, the term of this patent is extended or adjusted under 35 U.S.C. 154(b) by 0 days.

(21) Appl. No.: 13/046,795

(22) Filed: Mar. 14, 2011

(65) Prior Publication Data

US 2011/0172539 A1 Jul. 14, 2011

Related U.S. Application Data

(60) Provisional application No. 61/345,615, filed on May 18, 2010, provisional application No. 61/434,970, filed on Jan. 21, 2011, provisional application No. 61/434,979, filed on Jan. 21, 2011.

(51) Int. Cl.
*A61B 8/00* (2006.01)

(52) U.S. Cl.
USPC .......................... 600/437; 382/128; 600/450

(58) Field of Classification Search .......... 600/437–469; 382/130–132
See application file for complete search history.

(56) References Cited

U.S. PATENT DOCUMENTS

| | | | | |
|---|---|---|---|---|
| 5,315,512 | A * | 5/1994 | Roth | 600/442 |
| 5,923,770 | A * | 7/1999 | O'Donnell et al. | 382/131 |
| 6,106,466 | A * | 8/2000 | Sheehan et al. | 600/443 |
| 7,110,583 | B2 * | 9/2006 | Yamauchi | 382/128 |
| 7,542,622 | B1 * | 6/2009 | Angelini et al. | 382/275 |
| 7,567,696 | B2 * | 7/2009 | Moreau-Gobard et al. | 382/131 |
| 7,693,315 | B2 * | 4/2010 | Krishnan et al. | 382/128 |
| 7,693,563 | B2 * | 4/2010 | Suresh et al. | 600/407 |
| 7,813,537 | B2 * | 10/2010 | Epstein et al. | 382/128 |
| 7,889,912 | B2 * | 2/2011 | Orderud | 382/154 |
| 7,912,528 | B2 * | 3/2011 | Krishnan et al. | 600/407 |
| 8,131,043 | B2 * | 3/2012 | Binkley et al. | 382/131 |
| 8,144,957 | B2 * | 3/2012 | Qu et al. | 382/128 |
| 2004/0153128 | A1 * | 8/2004 | Suresh et al. | 607/14 |
| 2005/0020903 | A1 * | 1/2005 | Krishnan et al. | 600/407 |
| 2005/0059876 | A1 * | 3/2005 | Krishnan et al. | 600/407 |
| 2005/0254708 | A1 * | 11/2005 | Jolly et al. | 382/173 |
| 2007/0014452 | A1 * | 1/2007 | Suresh et al. | 382/128 |
| 2008/0069436 | A1 * | 3/2008 | Orderud | 382/154 |
| 2008/0253638 | A1 * | 10/2008 | Binkley et al. | 382/131 |
| 2009/0190813 | A1 * | 7/2009 | Qu et al. | 382/130 |
| 2011/0060576 | A1 * | 3/2011 | Sharma et al. | 703/11 |

* cited by examiner

*Primary Examiner* — Sanjay Cattungal
(74) *Attorney, Agent, or Firm* — Barry Choobin; Choobin & Choobin Consultancy

(57) ABSTRACT

The embodiments herein provide a method and a system for modeling left ventricle of heart for echocardiography machines. The method comprising the steps of taking a test case for performing echocardiography by a cardiac machine, obtaining echocardiography data from a plurality of myocardial segments, applying mathematical formulas for assumptions based on blood properties at a myocardial muscle sample and deriving coefficients of algebraic equations of quadratic forms from the mathematical formulas, calculating mathematical behavior of the myocardial muscle sample using the algebraic equations, estimating the left ventricle as a fabricated object using the quadratic forms and deriving a physical and mathematical model for the left ventricle. The echocardiography data of the myocardial muscle sample includes the velocity, displacement, strain rate and strain corresponding to the motion and deformation of the muscle volume sample having attached strain components to each myocardial muscle sample.

9 Claims, 13 Drawing Sheets

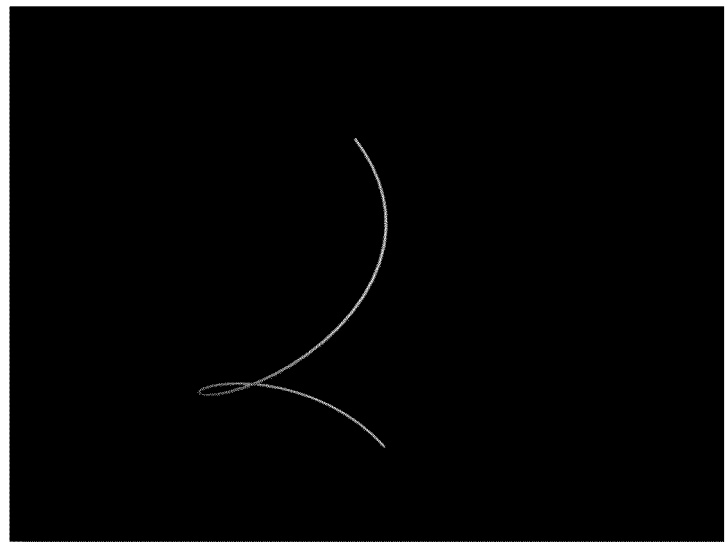
Fig. 4A
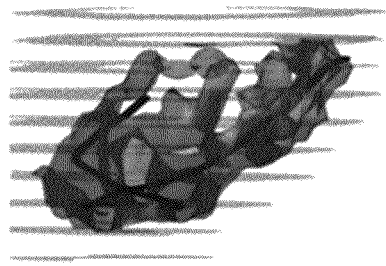
Fig. 4B
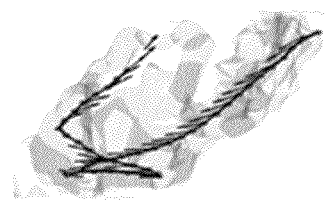
Fig. 4C
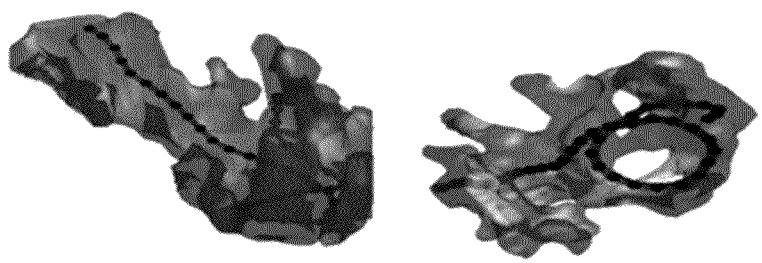
Fig. 4D
Fig. 4E

SYSTEM AND METHOD FOR MODELLING LEFT VENTRICLE OF HEART

CROSS-REFERENCE TO RELATED APPLICATIONS

This application claims the benefit of U.S. provisional patent application Ser. Nos. 61/345,615, filed May 18, 2010; 61/434,970 filed on Jan. 21, 2011; and 61/434,979 filed on Jan. 21, 2011, which are incorporated herein by reference in their entireties.

BACKGROUND

1. Technical Field

The embodiments herein generally relate to medical imaging systems and particularly to cardiac imaging systems. The embodiments herein more particularly relate to an echocardiography system and to a cardiac modeling system and method for modeling left ventricle of heart. The embodiments herein disclose a method and system for physical and mathematical modeling of the left ventricle in an echocardiography system.

2. Description of the Related Art

Cardiovascular disease is the leading cause of death in many countries. The mortality rate is decreased over the years as lifestyle has changed, but the reduction in mortality rate is also due to the development of new technologies to diagnose disease. One of these techniques is Magnetic Resonance Imaging (MRI) which provides time-varying three-dimensional image of the heart. Generally, the physicians examines the heart chambers, the endocardium and epicardium to measure changes in ventricular blood volume and wall thickening properties over a cardiac cycle to diagnose variation in cardiovascular functionalities. The left ventricle is of particular interest, since it pumps oxygenated blood out to distant tissue in the entire body.

The left ventricle is one of the chambers of the heart having a main role in the cardiac function. The left ventricle, being a muscular body, eases the realization of its function and dysfunction using cardiac imaging systems. The most common imaging tests used in cardiac medicine includes echocardiography/ultrasound of the heart, nuclear perfusion imaging, cardiac magnetic resonance imaging and cardiac computer tomography. An echocardiogram employs ultrasound to examine the functionality of the heart. In addition to a function of providing single-dimension images, known as M-mode echo, the system allows accurate measurement of the heart chambers. The two-dimensional (2-D) Echo is another imaging test for displaying a cross sectional cut of the beating heart, including the chambers, valves and blood vessels that exit from the left ventricle and the right ventricle.

The M-mode and 2-D Echo evaluate the size, thickness and movement of heart structures whereas Doppler assesses direction and velocity of the blood flow using ultrasound. Echocardiography provides information about the size of the chambers, pumping function, valve function whereas the tissue Doppler, myocardial velocity and displacement, strain and strain rate echocardiography provide a measure of the wall motion. Ultra sonograms are generally used as the imaging method, as they are widely available, inexpensive and non-invasive. However, ultrasonographic pictures are unclear, blurred and noisy thereby making the pictures difficult for an automatic analysis.

Hence there is a need for modeling of the left ventricle to study the normal and abnormal conditions of the left ventricle. Also there exists a need for modeling of the myocardium for evaluating the myocardial motions and velocities to characterize the regional contribution within the myocardium to the global function of the heart.

The abovementioned shortcomings, disadvantages and problems are addressed herein and which will be understood by reading and studying the following specification.

OBJECTS OF THE EMBODIMENTS

The primary object of the embodiments herein is to provide an elastic mathematical modeling of the left ventricle to study the normal and abnormal conditions of the heart.

Another object of the embodiments herein is to provide a mechanical and dynamic modeling of the myocardium for evaluating the myocardial motions and velocity of motion in a specific region of the heart.

These and other objects and advantages of the embodiments herein will become readily apparent from the following detailed description taken in conjunction with the accompanying drawings.

SUMMARY

The various embodiments herein provide a method for modeling left ventricle of heart for echocardiography machines mathematically and physically. The method comprises acquiring an echocardiography data from a plurality of myocardial segments, generating mathematical equations for deriving a secondary data for estimating blood properties from the acquired electrocardiography data, deriving coefficients of mathematical equations generated as algebraic equations of quadratic forms for each point on a myocardial segments, projecting behaviors of a myocardial muscle sample mathematically as a point on a quadratic surface, estimating behavior of a local part in a myocardium mathematically, estimating the left ventricle as a fabricated object by using the quadratic surfaces and deriving physical and mathematical model for the left ventricle from the fabricated object.

According to an embodiment herein, the derivation of coefficients for the quadratic forms includes calculating body force attached to the myocardial muscle sample on real time, calculating force of blood flow near the neighborhood of the muscle volume sample, calculating the velocity of the blood flow near the neighborhood of the muscle volume sample in the myocardium of the left ventricle, applying mathematical formula on the velocity of the blood flow near the neighborhood of the muscle volume sample, providing mathematical formula to compute strain rate and providing mathematical formula to compute strain.

According to an embodiment herein, the method of physical modeling of the left ventricle includes obtaining the echocardiography data from a myocardial muscle volume sample, deriving motion and deformation of the myocardial muscle volume sample having attached strain components, defining a flat and smooth map of fibers for the strain components and joining together the fibers to get the physical modeling of the left ventricle.

According to one embodiment herein, the echocardiography data from the muscle volume sample includes a velocity, a displacement, a strain and a strain rate. A displacement value is computed from the velocity data. The velocity data includes a radial velocity, longitudinal velocity and twist velocity. A strain rate is calculated from the computed displacement value. A strain value is calculated from the calculated strain rate.

According to one embodiment herein, the strain components of the muscle volume sample include a radial strain, a longitudinal strain and a circumferential strain.

According to one embodiment herein, a method for mathematical modeling of the left ventricle includes identifying a myocardial muscle sample volume, obtaining the echocardiography data by a cardiac machine in a echocardiograph, applying mathematical formulas for assumptions made for blood properties, identifying mathematical behavior of the muscle point in the myocardium and reconstructing the left ventricle mathematically by joining the curves.

According to one embodiment herein, a body force attached to the myocardial muscle sample is derived by calculating a motion and a deformation of the myocardial muscle sample.

According to one embodiment herein, a body force attached to the myocardial muscle sample is calculated by the mathematical formulas independently includes a radial body force, a longitudinal body force and a circumferential body force.

According to one embodiment herein, a system for modeling left ventricle includes a cardiac machine for collecting an echocardiography data and an echocardiography machine to run an application program for modeling the left ventricle. The echocardiography data from the cardiac machine is fed to the echocardiography machine, preloaded with the application program containing the codes for modeling the left ventricle physically and mathematically.

According to one embodiment herein, the application program for modeling the left ventricle physically and mathematically is a Mathlab software.

BRIEF DESCRIPTION OF THE DRAWINGS

The other objects, features and advantages will occur to those skilled in the art from the following description of the preferred embodiment and the accompanying drawings in which:

FIG. 4A-4E illustrate a schematic representation of a physical modeling of the left ventricle shown with fibers indicating the strain components, according to one embodiment herein.

Figure 1:
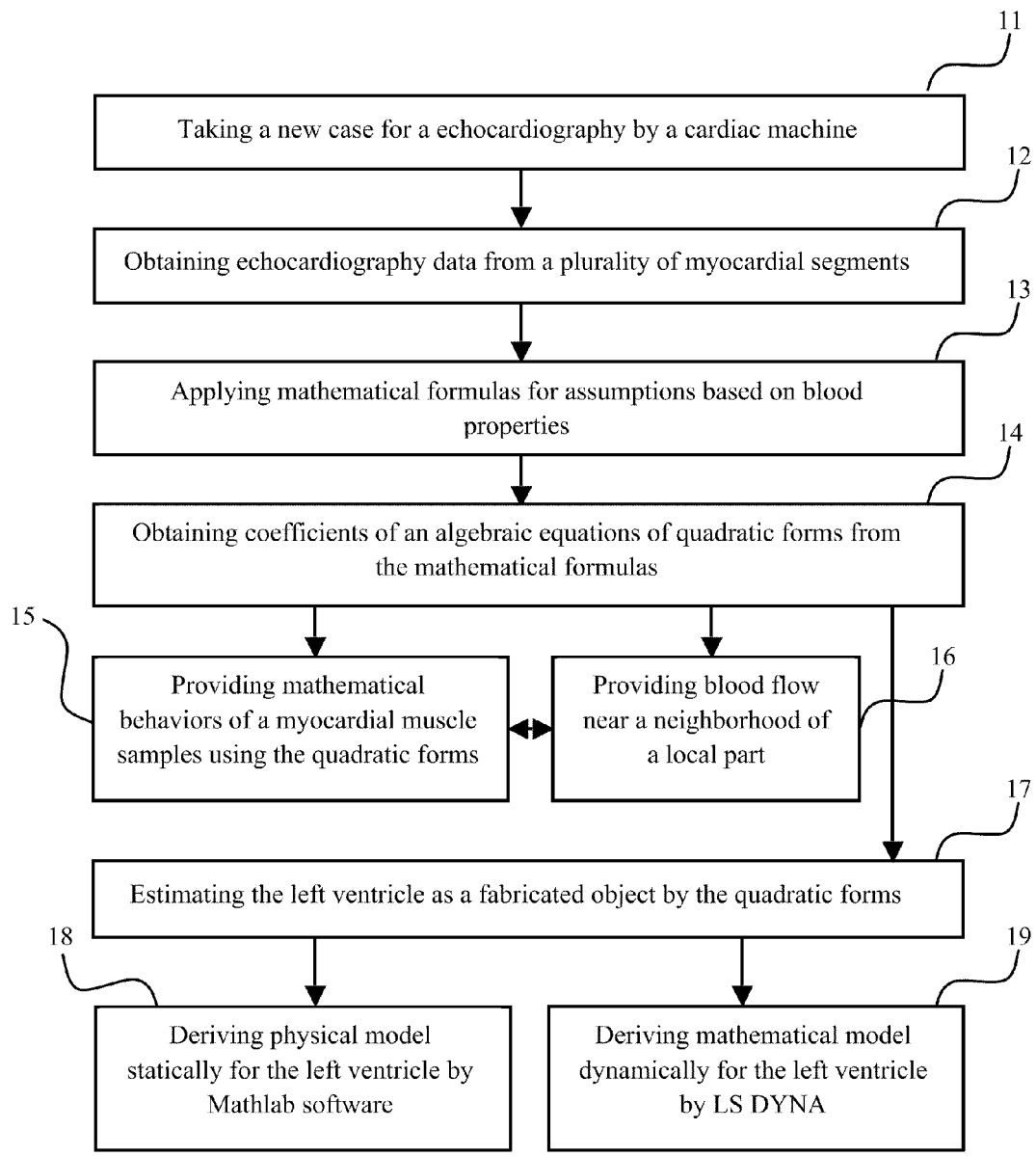
FIG. 1 illustrates a flowchart indicating a general method for modeling a left ventricle physically and mathematically for echocardiography machines, according to one embodiment herein.

Although the specific features of the embodiments herein are shown in some drawings and not in others. This is done for convenience only as each feature may be combined with any or all of the other features in accordance with the embodiments herein.

DETAILED DESCRIPTION OF THE EMBODIMENTS

In the following detailed description, a reference is made to the accompanying drawings that form a part hereof, and in which the specific embodiments herein that may be practiced is shown by way of illustration. These embodiments herein are described in sufficient detail to enable those skilled in the art to practice the embodiments herein and it is to be understood that the logical, mechanical and other changes may be made without departing from the scope of the embodiments herein. The following detailed description is therefore not to be taken in a limiting sense.

The embodiments herein provide a method for modeling a left ventricle of heart for echocardiography machines. The method comprises obtaining echocardiography data from a plurality of myocardial segments, applying mathematical formulas for assumptions based on blood properties, obtaining coefficients of an algebraic equations of quadratic forms from the mathematical formulas, providing mathematical behaviors of a myocardial muscle sample using the quadratic forms, obtaining blood flow velocity near a neighborhood of a myocardial sample in the myocardium of the left ventricle, estimating the left ventricle as a fabricated object by the quadratic forms and deriving physical and mathematical models for the left ventricle.

According to one embodiment herein, the derivation of coefficients for the quadratic forms includes calculating a body force attached to the myocardial muscle sample on real time, calculating a force of blood flow near a neighborhood of the muscle volume sample, calculating a velocity of the blood flow near the neighborhood of the muscle volume sample in the myocardium of the left ventricle, applying a mathematical formula on the velocity of the blood flow near the neighborhood of the muscle volume sample, providing a mathematical formula to compute a strain rate and providing a mathematical formula to compute a strain.

According to one embodiment herein, a method of physical modeling of a left ventricle includes obtaining an echocardiography data from a myocardial muscle volume sample, deriving motion and deformation of the myocardial muscle volume sample having attached strain components, defining a flat and smooth map of fibers for the strain components and joining together the fibers to get the physical modeling of the left ventricle.

According to one embodiment herein, the echocardiography data from the muscle volume sample includes a velocity, a displacement, a strain and a strain rate.

According to one embodiment herein, the strain components of the muscle volume sample include a radial strain, a longitudinal strain and a circumferential strain.

According to one embodiment herein, a method for mathematical modeling of a left ventricle includes identifying a myocardial muscle sample volume, obtaining the echocardiography data by a cardiac machine in a echocardiograph, applying mathematical formulas for assumptions made for blood properties, identifying mathematical behavior of the muscle point in the myocardium and reconstructing the left ventricle mathematically by joining the curves.

According to one embodiment herein, a body force attached to the myocardial muscle sample is derived by calculating a motion and a deformation of the myocardial muscle sample.

According to one embodiment herein, a body force attached to the myocardial muscle sample is calculated by the mathematical formulas independently for at least one of a radial body force, a longitudinal body force and a circumferential body force.

According to one embodiment herein, a system for modeling a left ventricle includes a cardiac machine for collecting an echocardiography data and an echocardiography machine to run an application program for modeling the left ventricle. The echocardiography data from the cardiac machine is fed to the echocardiography machine, preloaded with the application program containing the codes for modeling the left ventricle physically and mathematically.

According to one embodiment herein, an application program for modeling the left ventricle physically and mathematically is a Mathlab software.

FIG. 1 illustrates a flowchart for modeling a left ventricle physically and mathematically for echocardiography machines 10, according to one embodiment herein. The embodiments herein reconstruct a left ventricle physically and mathematically and then the result is applied to the echocardiography machines. The cardiac machine 11 takes a test case for an echocardiography as a reference for examination. The cardiac machine 11 obtains the echocardiography data from a plurality of myocardial segments 12 due to the motions and deformations of the myocardial segments. Using the data from the echocardiography, mathematical formulas are applied for the assumptions based on the blood properties 13. The assumptions are made with the following formula based on the blood properties:

$$=Pc, pPc, FPc, \text{Strain}i, j, fPc, vPc, VPc, \text{StrainRate}kl, Pc$$

From the mathematical formulas, the coefficients of algebraic equations of the quadratic forms are derived 14. The mathematical behaviors of a myocardial muscle samples are obtained 15 Using the quadratic form.

The mathematical behavior of the point Pc as a myocardial muscle sample on a quadratic surface which its algebraic form is $=ijxjxi\text{Strain}i,jPc$, The mathematical behavior of a myocardial muscle samples is provided along with the blood flow at a point on a quadratic surface 16 of the myocardial muscle sample for estimating the left ventricle as a fabricated object by the quadratic forms 17. After estimating the left ventricle as a fabricated object, the physical model for the left ventricle 18 is derived statically using Mathlab software and mathematical model for the left ventricle is derived dynamically using LS DYNA. The mathematical behavior of myocardial muscle samples using the quadratic forms provides for elastic modeling of the left ventricle.

Figure 2A:
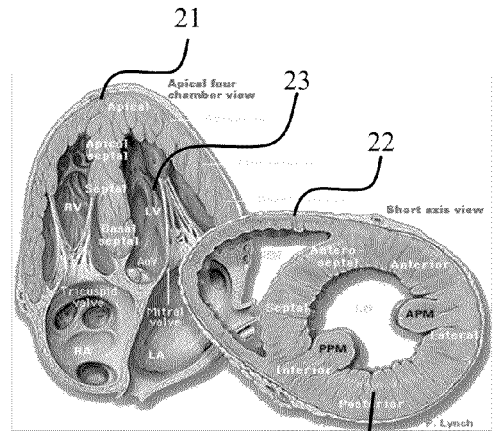
FIG. 2A-2D a physical modeling of the left ventricle toward a muscle volume sample on it and a mathematical modeling of the left ventricle toward the strain components attached to the muscle volume sample, according to one embodiment herein.
Figure 2B:
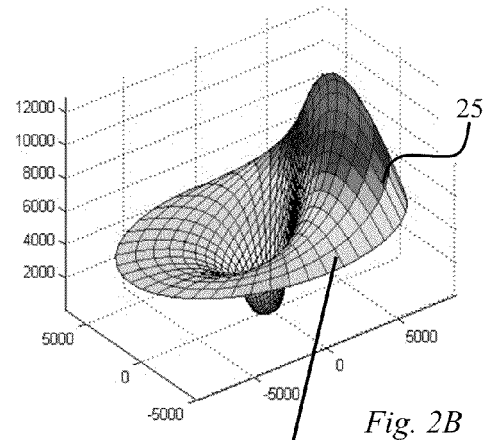
Figure 2C:
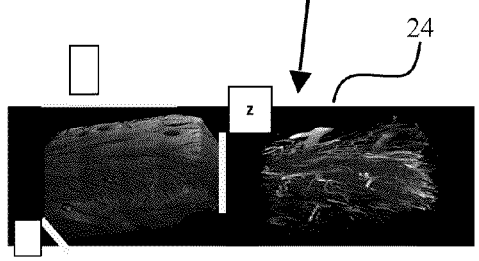
Figure 2D:
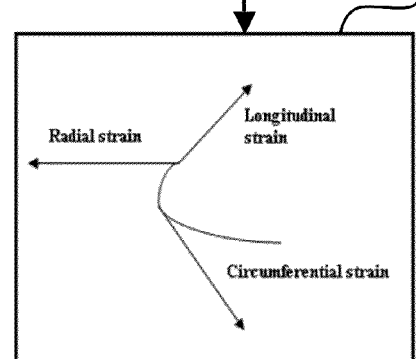

FIG. 2A-2B illustrates a physical modeling of the left ventricle toward a muscle volume sample and a mathematical modeling of the left ventricle toward the strain components attached to the muscle volume sample, according to one embodiment herein. The normal left ventricular myocardium is generally less than 12 mm thick at diastole-end, and is adapted to supply approximately 60 percent or more of the blood volume in the left ventricle 23. The apical four chamber view 21 and the mid-ventricle short axis view 22 provides for assessing left ventricular myocardial function as shown in FIG. 2C. FIG. 2D illustrates the myocardial muscle volume sample having components x, y, z with respect to the apex of the heart 24. The echocardiography data of a myocardial muscle includes velocity, displacement, strain rate and strain which represent the motion and deformation of the muscle volume sample. For each myocardial muscle sample having attached strain components such as a radial strain, longitudinal strain and circumferential strain, a flat and smooth map of fibers for strain components are provided by:

$$f=(x,xx)$$

A flat and smooth map of fibers for the strain components are defined and the fibers are joining together to get the physical modeling of the left ventricle.

FIG. 2B illustrates the mathematical modeling of the left ventricle 25. The myocardial muscle sample volume which includes the velocity and displacement and strain rate and strain that explain the motion and deformation of the muscle volume sample having attached strain components are identified. The strain components attached to a geometric point 26 is as shown in FIG. 2D. The mathematical formulas for assumptions made for blood properties are applied. The mathematical behavior of the muscle point in the myocardium is identified and the left ventricle is reconstructed mathematically by joining the fibers or curves.

Figure 3:
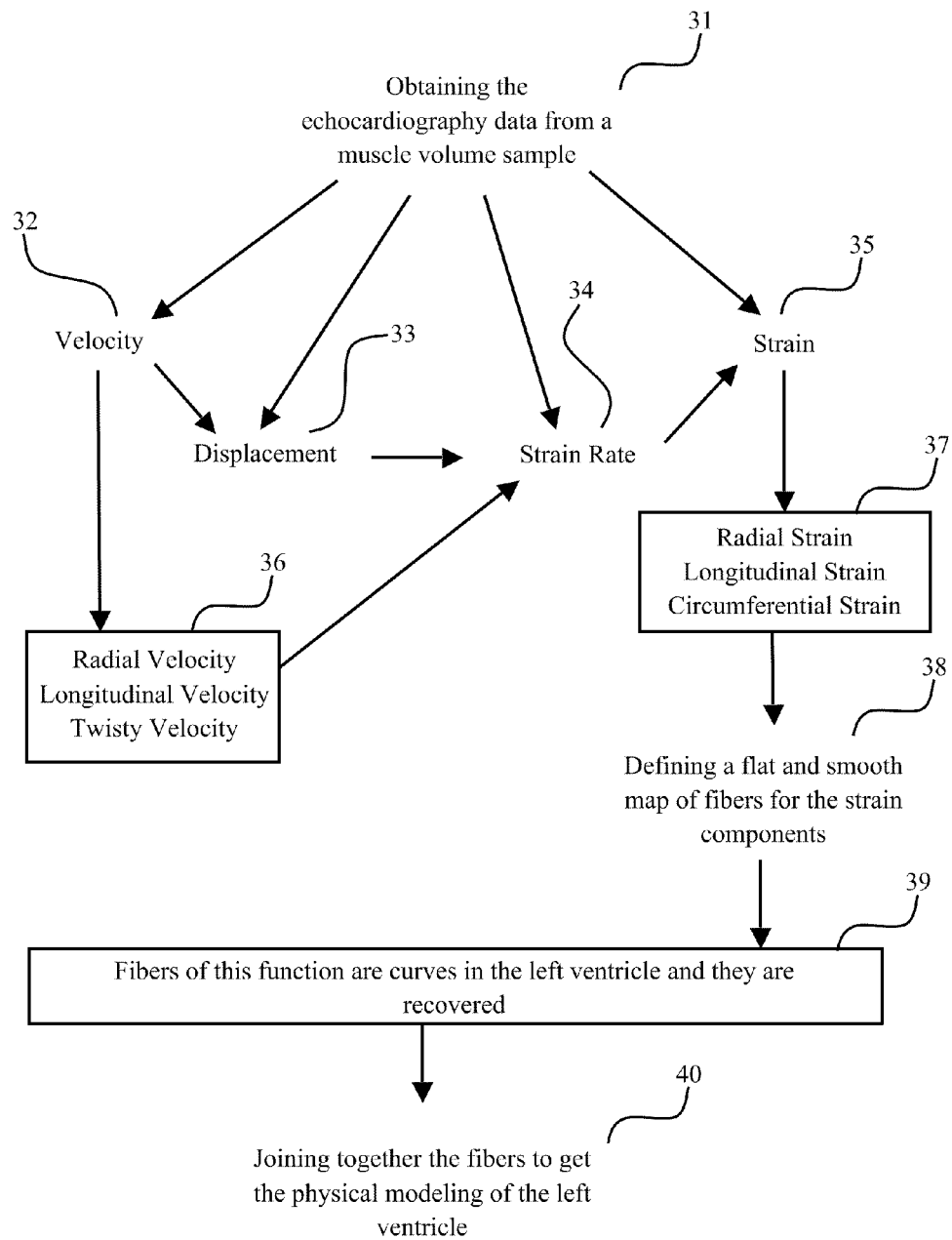
FIG. 3 illustrates a flowchart for a method for a physical modeling of the left ventricle statistically using ultrasound data from an echocardiography, according to one embodiment herein.

FIG. 3 illustrates a flowchart for a method for a physical modeling of the left ventricle statistically using ultrasound data from an echocardiography, according to one embodiment herein. The echocardiography data of a myocardial muscle is obtained 31 with respect to a test case. The echocardiography data of a myocardial muscle includes velocity 32, displacement 33, strain rate 34 and strain 35 that explain the motion and deformation of the muscle volume sample having attached strain components. The motion and deformation of the muscle volume sample is derived by calculating radial velocity, longitudinal velocity and twisty velocity 36. The strain components attached to the muscle volume sample includes radial strain, longitudinal strain and circumferential strain 37. To each myocardial muscle sample a flat and smooth map of stain components is derived 38 by the following function:

$$f=(x,xx)$$

For the derived flat and smooth map of stain components, f−1(*,*={thosemyocardialmusclesamplesthatgoto*,*under f} are those sets which are followed by a coded algorithm in Mathlab software. By gluing and joining these fibers together, the physical modeling of the left ventricle statically is derived 40.

FIG. 4 illustrates a physical modeling of the left ventricle and fibers of the map as curves in the myocardium of the left ventricle, according to one embodiment herein. Echocardiography data of a myocardial muscle sample include the velocity, the displacement, the strain rate and the strain to explain the motion and deformation of the muscle volume sample having attached strain components. For each of the myocardial muscle sample, a flat and smooth map is derived as shown in FIG. 4A-4E. The physical modeling of the left ventricle and the fibers of the map f as curves in the myocardium of the left ventricle and using quadratic forms provides for mathematical approximation of the curves/fibers.

Figure 5:
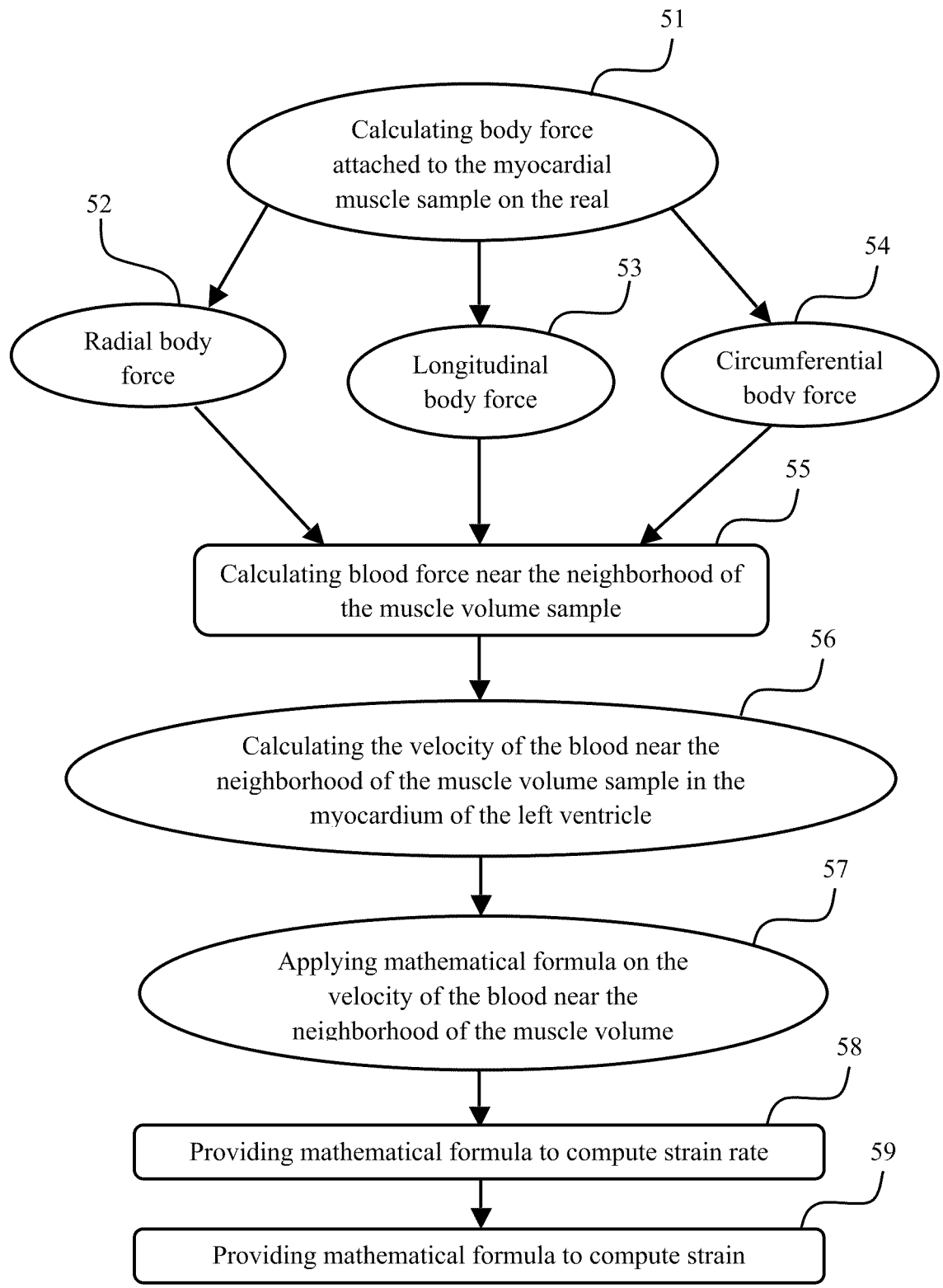
FIG. 5 illustrates a flowchart for a method for deriving mathematical formulae for strain and strain rate using a mathematical model, according to one embodiment herein.

FIG. 5 illustrates a flowchart for deriving the coefficients for quadratic forms to approximate fibers/curves mathematically, according to one embodiment herein. The body force created due to the motion and deformation of the to the myocardial muscle sample on the real time 51 is calculated. The body force includes radial body force 52, longitudinal body force and circumferential body force 54. The blood force near the neighborhood of the muscle volume sample 55 is also calculated. The velocity of the blood near the neighborhood of the myocardial muscle volume sample in the myocardium of the left ventricle 56 is also calculated. The mathematical formula on the velocity of the blood near the neighborhood of the muscle volume sample is applied 57. The mathematical formula to compute strain rate 58 and the mathematical formula to compute strain is then derived 59. For a myocardial muscle volume sample Pc which has been located on a fiber of the map f like, the motion and deformation is followed during the end of diastole to the end of systole. After an elapse of time "t" since the end of a diastole, radial strain rate for the fiber PkPl on the curve is:

$$\epsilon'Pk,Pl=VPkt-VPl(t)/LPkPl(t).$$

Let Dt,Pc and Wr,t,Pc are displacement and velocity of the myocardial muscle volume sample at a time t.

By classical mechanic we set:

$$Dt+LABt-L(t0)=12ar,tt2+Wr,tt,$$

where t0 is the time and L(t0) is the length of the fiber AB respectively at the end of diastole. Using the 1-D deformation, above formula is rewritten as:

$$Dtt+LABtt-Lt0t=12ar,tt+Wr,t$$

By measuring radial strain rate and strain of the fiber AB at time "t":

$$Dt,Pct+err,Pc't\cdot errPc,t+1Lt0=12ar,t,Pct+Wr,tPc,$$

Thus reformulate at can be formulated as below:

$$ar,t=2Dtt2+2err't\cdot errt+1Lt0t-2Wr,tt$$

Now if μ be the density and volume (t) be the volume respectively of the myocardial muscle volume sample after the contraction during the time "t". The radial force which need to be provided to result in this motion and deformation at time "t" is:

$$FPcr,t=\mu\cdot\text{Volume}(t)\cdot ar,t$$

Similarly the longitudinal force (Fl,t) and circumferential force (Fc,t) formulas are obtained like the radial force.

The Longitudinal Force (Fl,t) which needed to result in this motion and deformation at time "t" is:

$$FPcl,t=\mu\cdot\text{Volume}(t)\cdot al,t$$

The Circumferential Force (Fc,t) which is needed to result in this motion and deformation at time "t" is:

$$FPcc,t=\mu\cdot\text{Volume}(t)\cdot ac,t$$

Let:

$$FPc,t2=FPc,r,t2+FPc,l,t2+FPc,c,t2$$

be the absolute value of the body force of a myocardial muscle sample on the real time from the end of diastole to the end of systole and let (x1,x2,x3,t) be the coordinate system of the red blood cell in a neighborhood Ω of a myocardial muscle sample Pc. Then the "blood force" of the red blood cell at region Ω is formulated by the following formula:

$$fPc,t=\Omega FPc,t(p,q,s)\otimes\delta(x1,x2,x3,t)dx$$

where $\delta(x1,x2,x3,t)=\delta^*x1,t\cdot\delta^*x2,t\cdot\delta^*x3,t$, $\delta^*$ is the direct function and (p,q,s) is the polar coordinate of the myocardial muscle sample Pc with respect to the apex of the heart and x=(x1,x2,x3) and components of fPc,t are:

$$fPc,r,t=\Omega FPc,r,t(p,q,s)\otimes\delta(x1,x2,x3,t)dx$$

$$fPc,l,t=\Omega FPc,l,t(p,q,s)\otimes\delta(x1,x2,x3,t)dx$$

$$fPc,c,t=\Omega FPc,c,t(p,q,s)\otimes\delta(x1,x2,x3,t)dx$$

The red blood cell velocity in the neighborhood Ω of Pc is formulated as $$vPc,t=totfPc,tdt,$$

where:

$$vPc,r,t=totfPc,r,tdt$$

$$vPc,l,t=totfPc,l,tdt$$

$$vPc,c,t=totfPc,c,tdt$$

The velocity induced by the red blood cell to point Pc is formulated as:

$$VPc,t=\Omega vPc,t\otimes\delta(x1,x2,x3,t)dx$$

Where the components include:

$$VPc,r,t=\Omega vPc,r,t\otimes\delta(x1,x2,x3,t)dx$$

$$VPc,l,t=\Omega vPc,l,t\otimes\delta(x1,x2,x3,t)dx$$

$$VPc,c,t=\Omega vPc,c,t\otimes\delta(x1,x2,x3,t)dx$$

The strain rate is formulated by:

$$\epsilon'Pl,Pk=VPk,t-VPl,t/LPl,Pk,$$

where Pk and Pl are points on in Ω the components of ε'k,l are:

$$\epsilon rr'Pk,Pl=VPk,r,t-VPl,r,t/LPk,Pl$$

$$\epsilon ll'Pk,Pl=VPk,l,t-VPl,l,t/LPk,Pl$$

$$\epsilon cc'Pk,Pl=VPk,c,t-VPl,c,t/LPk,Pl$$

The strain at point Pc is also computed by:

$$\epsilon Pc=(k,l\epsilon'Pl,Pkdt)$$

where its components are:

$$\epsilon rrPc=(k,l\epsilon rr'Pk,Pldt)$$

$$\epsilon llPc=(k,l\epsilon ll'Pk,Pldt)$$

$$\epsilon ccPc=(k,l\epsilon cc'Pk,Pldt)$$

Finally which passes from Pc in the region Ω is replaced by a curve, which its algebraic form is:

$$Q((y1,y2,y3))=\epsilon rr,Y\cdot y12+\epsilon ll,Y\cdot y22+\epsilon cc,Y\cdot y32$$

where Y=(y1,y2,y3) is the Cartesian coordinate of a point on in the region Ω.

Figure 6:
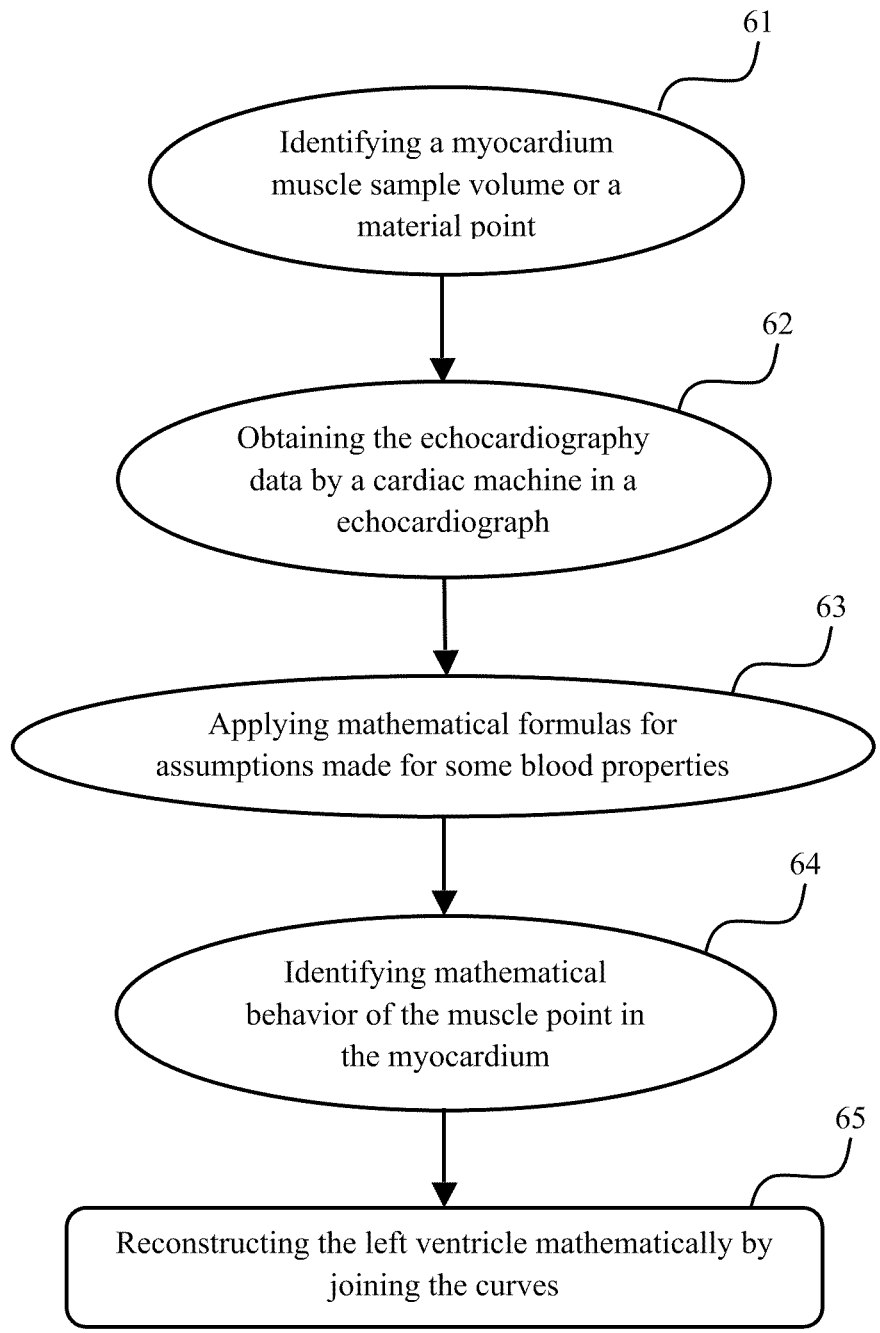
FIG. 6 illustrates a flowchart for a method for modeling a left ventricle mathematically, according to one embodiment herein.

FIG. 6 illustrates a flowchart of the mathematical modeling 60 of the left ventricle by curves on it, according to one embodiment herein. A material point or the muscle volume sample in the myocardium is identified 61. The motion and deformation is measured from the end of diastole to the end of systole for the myocardial muscle volume sample located on the fiber. The cardiac machine gets the echocardiography data from a plurality of myocardial segments due to the motions and deformations of the myocardial segments 62. Using the data from the echocardiography, mathematical formulas are applied for the assumptions based on the blood properties 63. The assumptions are made with the following formula based on the blood properties:

$$=Pc,pPc,FPc,Strain i,j,fPc,vPc,VPc,StrainRate kl,Pc$$

From the mathematical formulas, the coefficients of algebraic equations of the quadratic forms are derived as illustrated in FIG. 4. Using the quadratic forms, the mathematical behaviors of the material point or the myocardial muscle samples are obtained 64.
The mathematical behavior of the point Pc as a myocardial muscle sample on a quadratic surface which its algebraic form is =ijxjxiStraini,jPc, The mathematical behaviors of a myocardial muscle samples are provided along with the blood flow near a neighborhood of a local part for estimating the left ventricle as a fabricated object by the quadratic forms. After estimating the left ventricle as a fabricated object, the physical model for the left ventricle is derived statically and mathematical model for the left ventricle is derived mathematically 65.

Figure 7A:
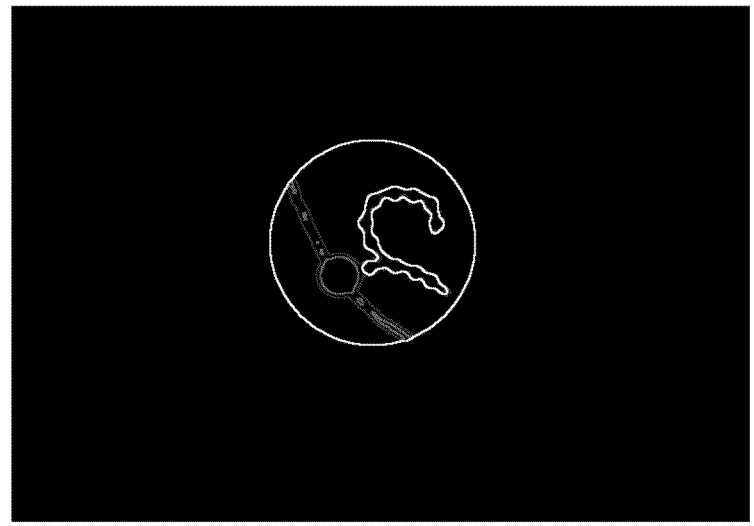
FIG. 7A illustrates a neighborhood of a myocardial muscle sample at the end of diastole, according to one embodiment herein.
Figure 7B:
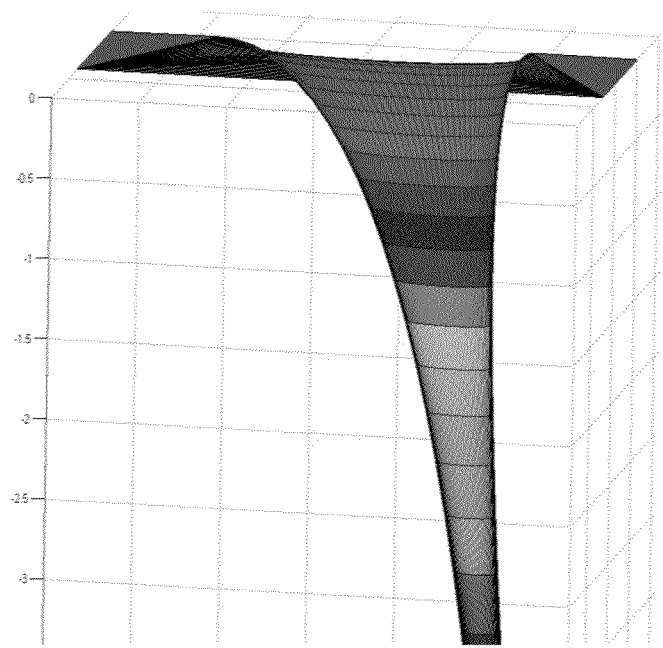
FIG. 7B illustrates a schematic mathematical representation of the left ventricle at the end of diastole, according to one embodiment herein.

FIG. 7A-7B illustrates a neighborhood of a myocardial muscle sample and a schematic mathematical representation of the left ventricle at the end of diastole, according to one embodiment of the present disclosure. The blood flow near a neighborhood of the local part are provided along with the myocardial muscle samples for estimating the left ventricle as a fabricated object by the quadratic forms as shown in FIG. 7A. After estimating the left ventricle as a fabricated object, the mathematical model for the left ventricle is derived mathematically by observing the semantic mathematical representation of the left ventricle at the end of diastole as shown in FIG. 7B.

Figure 8A:
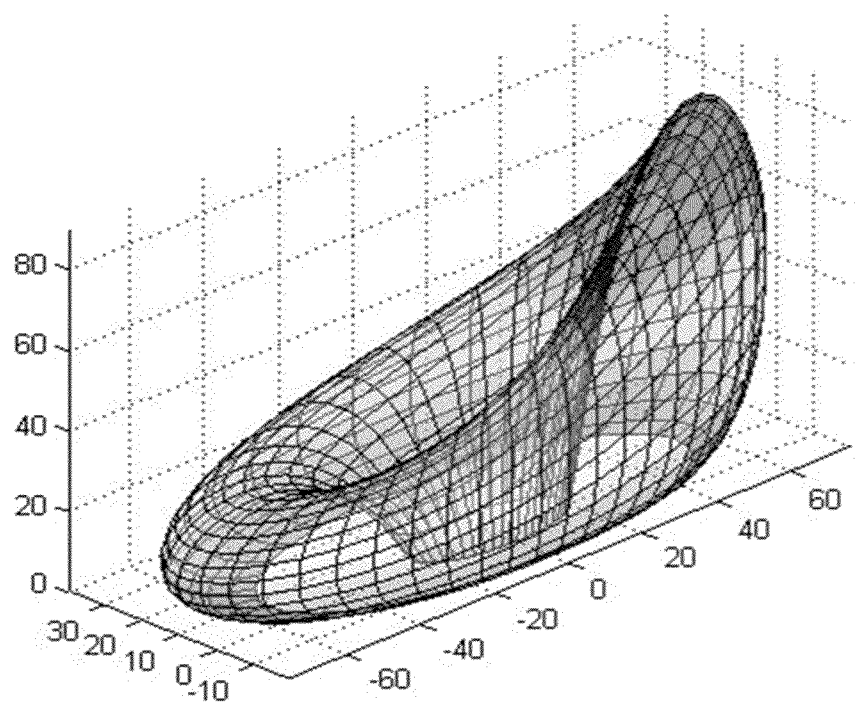
FIG. 8A-8B illustrates the process of mathematically reconstructing the left ventricle, according to one embodiment herein.
Figure 8B:
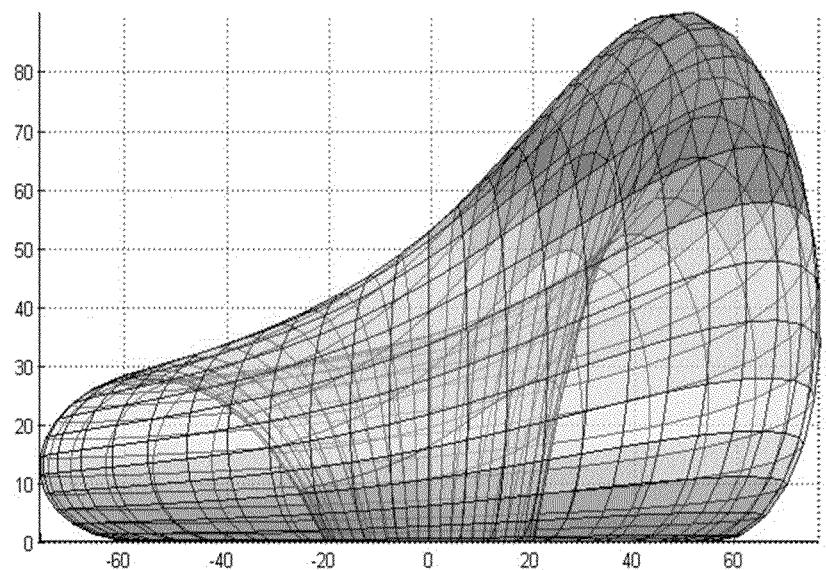

FIG. 8A-8B illustrates the process of mathematically reconstructing the left ventricle by curves on it, according to one embodiment of the present disclosure. The echocardiography data of a myocardial muscle sample is obtained. The echocardiography data of a myocardial muscle includes the velocity, displacement, strain rate and strain that explain the motion and deformation of the muscle volume sample having attached strain components. The motion and deformation of the muscle volume sample is derived by calculating radial velocity, longitudinal velocity and circumferential velocity. To each myocardial muscle sample a flat and smooth map of stain components is derived by the following function:

$$f=(x,xx)$$

The derived flat and smooth map of strain components, f-1(*,*={thosemyocardialmusclesamplesthatgoto*,*under f} are followed by a coded algorithm in Mathlab software. Fibers of this function are curve in the left ventricle. By gluing and joining together the fibers the physical modeling of the left ventricle is statically derived. Referring to the physical modeling of the left ventricle and fibers of the map f as curves in the myocardium of the left ventricle and using the quadratic forms, the fibers (curves) are approximated mathematically as shown in FIG. 8A-8B.

Figure 9A:
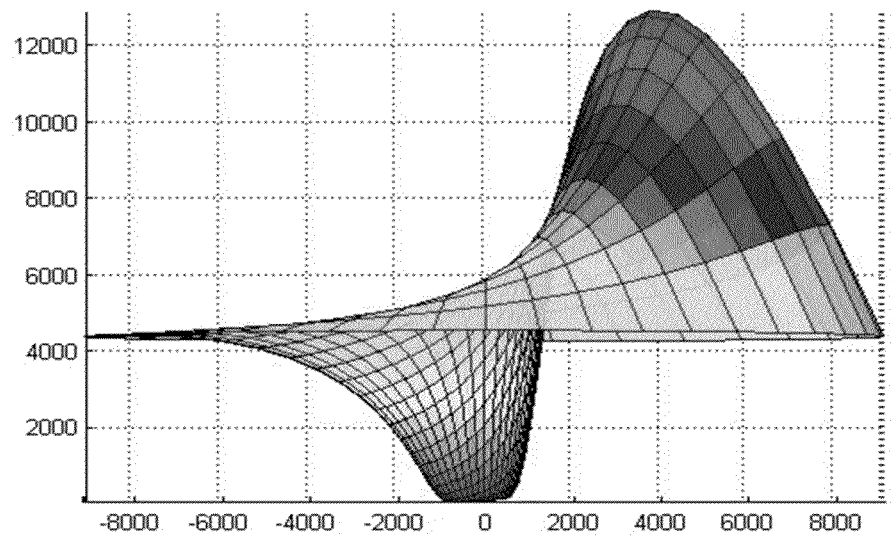
FIG. 9A illustrates a front view of a left ventricle indicating motion at the end of diastole of the myocardial muscle sample using gluing curves, according to one embodiment herein.
Figure 9B:
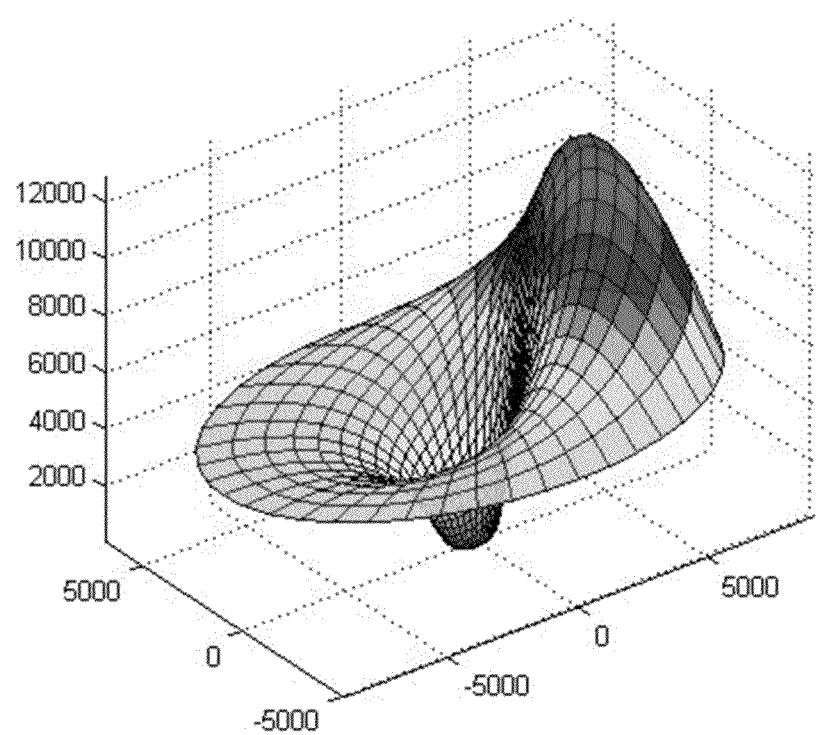
FIG. 9B illustrates a top view of a left ventricle indicating motion at the end of diastole of the myocardial muscle sample using gluing curves, according to one embodiment herein.

FIG. 9A-9B illustrates a front view and top view of the left ventricle showing the process of gluing curves of the myocardial muscle sample's motion at the end of diastole, according to one embodiment of the present disclosure. For each myocardial muscle sample, a flat and smooth map of strain components is derived.

For the derived flat and smooth map of strain components, fibers of the map f-1(*,*={thosemyocardialmusclesamplesthatgoto*,*under f} are followed by a coded algorithm in Mathlab software. Fibers of this function are curve in the left ventricle. By gluing and joining together these fibers the physical modeling of the left ventricle statically is derived. Referring to the physical modeling of the left ventricle and fibers of the map f as curves in the myocardium of the left ventricle and using the quadratic forms, the fibers (curves) are approximated mathematically as shown in FIG. 9A-9B.

Figure 10A:
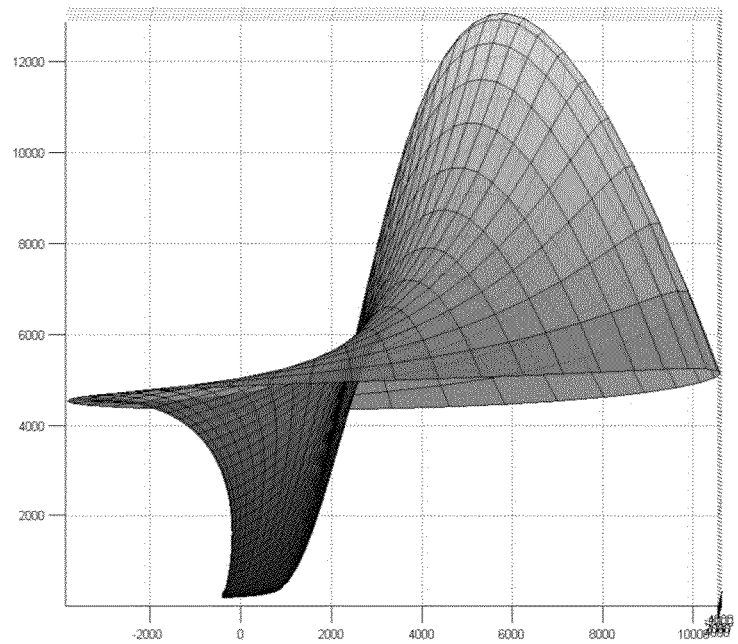
FIG. 10A illustrates a schematic mathematical representation of a front view of a left ventricle, according to one embodiment herein.
Figure 10B:
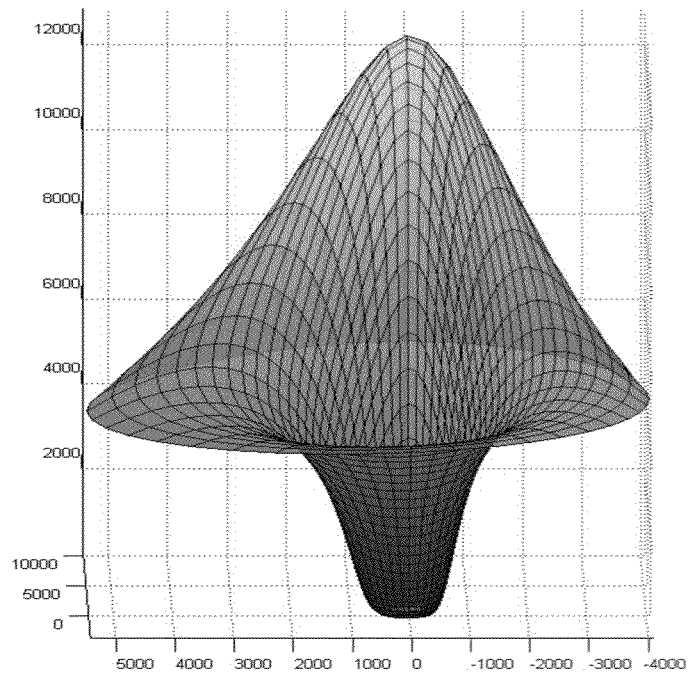
FIG. 10B illustrates a schematic mathematical representation of a top view of a left ventricle, according to one embodiment herein.

FIG. 10A-10B illustrates a front perspective view and side perspective view of the schematic mathematical representations of the left ventricle, according to one embodiment of the present disclosure. The gluing and joining of fibers leads to the physical modeling of the left ventricle statically. Then by using the quadratic forms on the physical modeling of the left ventricle and fibers of the map f as curves in the myocardium of the left ventricle, the fibers (curves) of the left ventricle are represented mathematically as shown in FIG. 10A-10B.

Figure 11A:
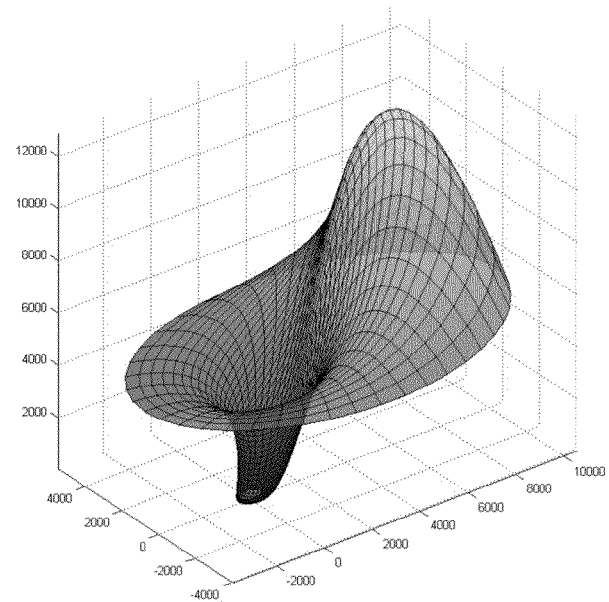
FIG. 11A-11B illustrates a left ventricle as a fibered object in three dimensional in the Mathlab software, according to one embodiment of the present disclosure.
Figure 11B:
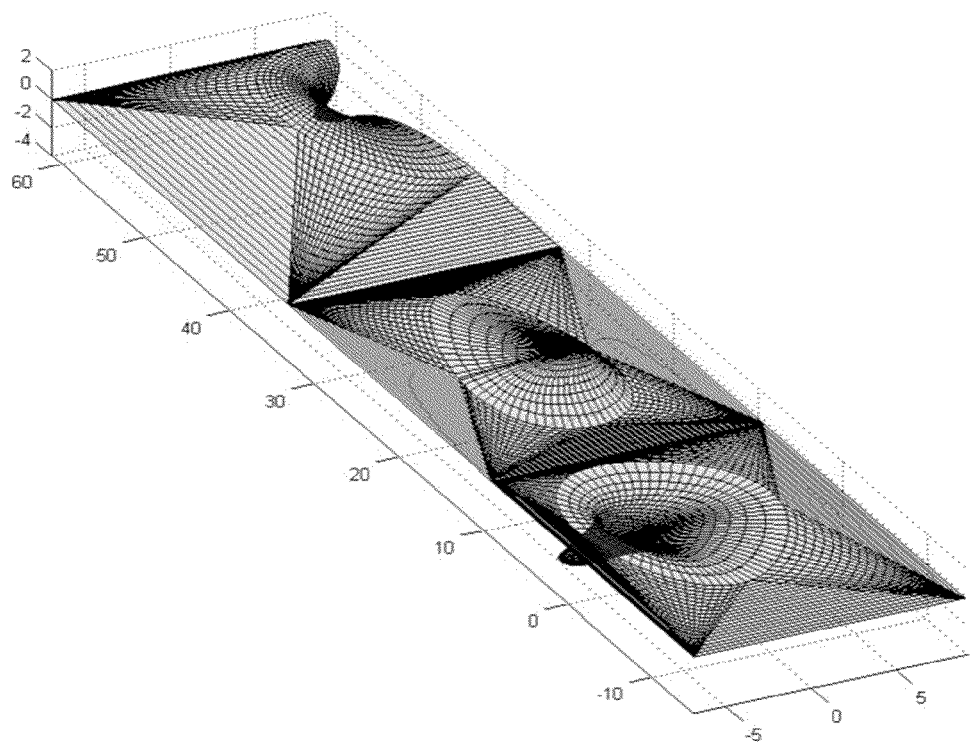

FIG. 11A-11B illustrates a three dimensional view of the left ventricle as a fibered object in the Mathlab software, according to one embodiment of the present disclosure. The mathematical behaviors of a myocardial muscle samples are provided along with the blood flow near a neighborhood of a local part for estimating the left ventricle as a fabricated object by the quadratic forms. The estimation of the left ventricle as a fabricated object in three dimensional in the mathlab software is as shown in FIG. 11A-11B. After estimating the left ventricle as a fabricated object, the physical model for the left ventricle is derived statically by a coded algorithm in the Mathlab software and mathematical model for the left ventricle is derived mathematically.

Figure 12A:
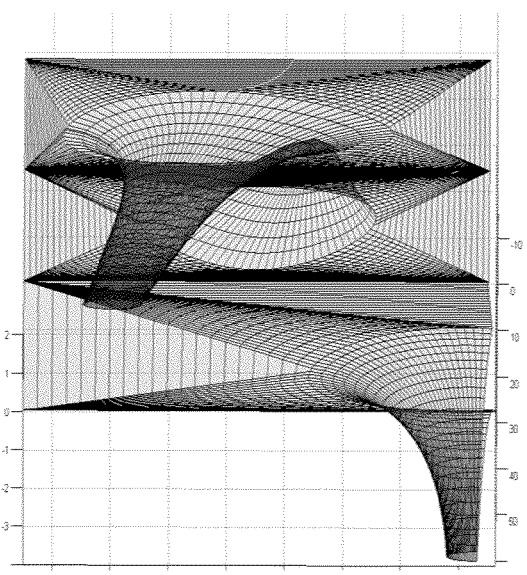
FIG. 12A-12B illustrates a left ventricle as a mathematical fibered object, according to one embodiment of the present disclosure.
Figure 12B:
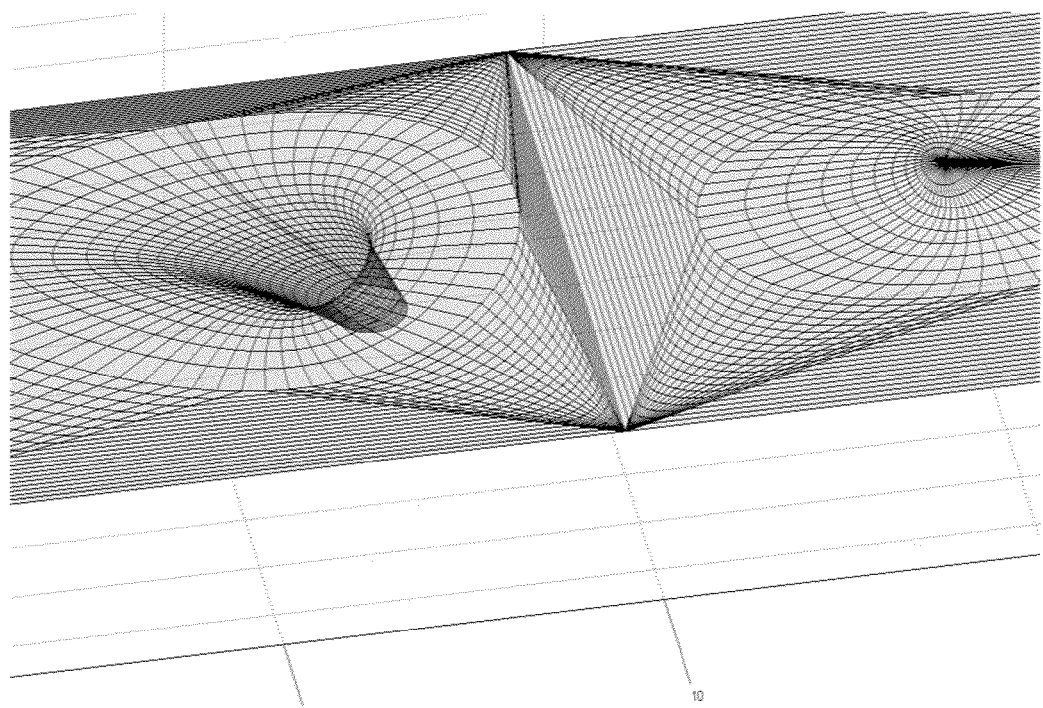

FIG. 12A-12B illustrates the perspective views of the left ventricle as a mathematical fibered object, according to one embodiment of the present disclosure. The left ventricle is estimated as the fabricated object in the mathlab software for deriving the physical model of the left ventricle. By applying the quadratic forms on the resulted physical model of the left ventricle and curves in the myocardium of the left ventricle, the mathematical model is derived and the complicated mathematical fibered object of the left ventricle is as shown in FIG. 12A-12B.

Figure 13:
FIG. 13 illustrates a mathematical modeling of a left ventricle indicating a histological representation of the left ventricle, according to one embodiment of the present disclosure.

FIG. 13 illustrates a mathematical modeling of the left ventricle showing a histological representation of the left ventricle, according to one embodiment of the present disclosure. The left ventricle is estimated as the fabricated object in the mathlab software for deriving the physical model of the left ventricle. By applying the quadratic forms on the resulted physical model of the left ventricle and curves in the myocardium of the left ventricle, the mathematical model is derived. The histological representation of the left ventricle helps to study the microscopic anatomy of cells and tissues of the left ventricle by examining a thin slice (section) of tissue under a light microscope or electron microscope. The ability to visualize or differentially identify microscopic structures is frequently enhanced through the use of histological stains.

The investigated algebraic curves according to the embodiments herein can be applied as a dynamic property of a polymer in an artificial left ventricle. The embodiments herein can be utilized to evaluate the left heart diseases by the modifications at those algebraic curves that have been formulized. The investigated curves can be represented in a computer and they can also be applied in the echocardiography machines. This provides for new technology in the cardiac imaging which reduces the need for highly experienced persons for operating machines for diagnosis of heart diseases.

As the investigated curves are showing pathological pathways in the myocardium of the left ventricle and have also been coded as a computer programming, the algorithm can be applied on the other medical devices and robotic surgeons with an interface.

The embodiment according to the present disclosure is adapted to solve the fluid dynamic in the left ventricle by using the mathematical modeling of the present disclosure.

The method of the present embodiments can be advanced for the other cavities of the heart. And also the present method introduces a new method in approximation theory.

The foregoing description of the specific embodiments will so fully reveal the general nature of the embodiments herein that others can, by applying current knowledge, readily modify and/or adapt for various applications such specific embodiments without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. Therefore, while the embodiments herein have been described in terms of preferred embodiments, those skilled in the art will recognize that the embodiments herein can be practiced with modification within the spirit and scope of the appended claims.

Although the embodiments herein are described with various specific embodiments, it will be obvious for a person skilled in the art to practice the disclosure with modifications. However, all such modifications are deemed to be within the scope of the claims.

It is also to be understood that the following claims are intended to cover all of the generic and specific features of the embodiments described herein and all the statements of the scope of the embodiments which as a matter of language might be said to fall there between.

What is claimed is:

1. A method for modeling a left ventricle, the method comprising the steps of:
    obtaining an echocardiography data from a plurality of myocardial segments;
    applying a plurality of mathematical formulas for assumptions on blood properties and wherein the plurality of mathematical formulas for assumptions on blood properties are $P_c$, $p_c$, $Fp_c$, $Strain_{i,j}$, $fp_c$, $vp_c$, $Vp_c$, $StrainRate_{ki, Pc}$, and wherein Pc is a point at a myocardial muscle sample on a quadratic surface, and wherein $p_c$ is a point at a neighborhood of the point Pc and wherein $Fp_c$ is the radial force at the point Pc, and wherein $fp_c$ is the blood force of the red blood cells at a neighborhood of the point Pc and wherein Vpc is the red blood cell velocity at the point Pc and wherein $vp_c$ is the red blood cell velocity at a neighborhood of the point Pc;
    deriving a plurality of coefficients of an algebraic equation of quadratic forms from the plurality of mathematical formulas, and wherein the algebraic equation of the quadratic form is $\Sigma_i^j x_j x_i Strain_{i,jP_c}$;
    providing a mathematical behavior of a myocardial muscle sample using the algebraic equation of quadratic forms;
    generating a left ventricle as a fabricated object using the algebraic equation of quadratic forms; and
    providing a physical model and a mathematical model for the left ventricle.

2. The method according to claim 1, wherein the step of deriving the plurality of coefficients for the quadratic forms comprises:
    calculating a body force attached to the myocardial muscle sample;
    calculating a force of blood flow near a neighborhood of the myocardial muscle sample;
    calculating a velocity of blood flow near the neighborhood of the myocardial muscle sample of the left ventricle;
    applying a first mathematical formula on the velocity of blood flow near the neighborhood of the myocardial muscle sample and wherein the first mathematical formula for calculating the velocity of blood flow near the neighborhood of the myocardial muscle sample is $v_{P_cx} = \int_{t_o}^{t} f_{P_c,t} \, dt$;
    providing a second mathematical formula to compute a strain rate, and wherein the second mathematical formula for computing a strain rate is $\epsilon'_{P_l P_k} = V_{P_k x} - V_{P_l x}/L_{P_l, P_k}$ and wherein $P_k$ and $P_l$ are points on a curve representing a myocardial muscle volume sample;
    providing a third mathematical formula to compute a strain, and wherein third mathematical formula for computing a strain is $z_{P_c} = (\Sigma_{k,l} \epsilon'_{P_l P_k} \, dt)$.

3. The method according to claim 1, wherein the step of providing the physical model of the left ventricle comprises:
    obtaining the echocardiography data from a myocardial muscle sample;
    deriving a motion and a deformation of the myocardial muscle volume sample having attached strain components;
    defining a flat and smooth map of fibers for the strain components; and
    joining the fibers together to get the physical model of the left ventricle.

4. The method according to claim 1, wherein the echocardiography data comprises at least one of a velocity, a displacement, a strain and a strain rate of motion and deformation of the myocardial muscle sample.

5. The method according to claim 3, wherein the strain components of the myocardial muscle sample includes a radial strain, a longitudinal strain and a circumferential strain.

6. The method according to claim 1, wherein the step of providing the mathematical model of the left ventricle comprises:
    identifying a myocardium muscle sample volume;
    obtaining the echocardiography data by a cardiac machine in a echocardiograph;
    applying the plurality of mathematical formulas;
    identifying mathematical behavior of the muscle point in the myocardium; and
    reconstructing the left ventricle mathematically by joining the curves.

7. The method according to claim 1, wherein the body force attached to the myocardial muscle sample is derived by calculating a motion and a deformation of the muscle volume sample.

8. The method according to claim 1, wherein the body force attached to the myocardial muscle sample is calculated independently for at least one of a radial body force, a longitudinal body force and a circumferential body force.

9. A system for modeling a left ventricle, the system comprising;

a cardiac machine adapted for collecting an echocardiography data; and
an echocardiography machine configured to run an application program for modeling the left ventricle;
wherein the echocardiography machine is configured to perform the method steps of claim 1, for modeling the left ventricle physically and mathematically.

* * * * *